United States Patent
Sato et al.

(10) Patent No.: US 8,536,470 B2
(45) Date of Patent: Sep. 17, 2013

(54) BODY COMPOSITION MONITOR THAT CORRECTS A BODY COMPOSITION EVALUATION BY COMPARING IT WITH A USER'S CHANGE IN WEIGHT READING TO CANCEL ERRORS CAUSED BY DRYNESS OF HANDS AND WAY OF GRIPPING

(75) Inventors: Tetsuya Sato, Kyoto (JP); Shinya Tanaka, Kyoto (JP); Yumi Kitamura, Kyoto (JP)

(73) Assignee: Omron Healthcare Co., Ltd., Kyoto-shi (JP)

( * ) Notice: Subject to any disclaimer, the term of this patent is extended or adjusted under 35 U.S.C. 154(b) by 545 days.

(21) Appl. No.: 12/866,808

(22) PCT Filed: Mar. 16, 2009

(86) PCT No.: PCT/JP2009/055010
§ 371 (c)(1),
(2), (4) Date: Aug. 9, 2010

(87) PCT Pub. No.: WO2009/116483
PCT Pub. Date: Sep. 24, 2009

(65) Prior Publication Data
US 2010/0331629 A1 Dec. 30, 2010

(30) Foreign Application Priority Data
Mar. 18, 2008 (JP) ................................. 2008-069168

(51) Int. Cl.
*A61B 5/05* (2006.01)
*A61B 5/053* (2006.01)
*G01G 19/40* (2006.01)

(52) U.S. Cl.
USPC ..................... 177/25.13; 177/25.19; 177/177; 177/245; 600/547

(58) Field of Classification Search
USPC ............ 177/25.13, 25.19, 177, 245; 600/547
See application file for complete search history.

(56) References Cited

U.S. PATENT DOCUMENTS

| | | | |
|---|---|---|---|
| 4,650,014 | A | 3/1987 | Oldendorf et al. |
| 5,817,031 | A | 10/1998 | Masuo et al. |

(Continued)

FOREIGN PATENT DOCUMENTS

| | | |
|---|---|---|
| CN | 1669523 A | 9/2005 |
| DE | 102 05 823 A1 | 8/2003 |

(Continued)

OTHER PUBLICATIONS

International Search Report issued in Application No. PCT/JP2009/055010; Dated Jun. 2, 2009 (With Translation).

(Continued)

*Primary Examiner* — Randy W Gibson
(74) *Attorney, Agent, or Firm* — Oliff & Berridge, PLC (57) ABSTRACT

A body composition monitor of the present invention includes means for measuring a body composition, means for storing a measured body composition value, and body composition comparison means for comparing the measured body composition value and a stored body composition value, in which the body composition monitor further includes means for inputting a body weight value, means for storing an inputted body weight, body weight comparison means for comparing the inputted body weight and stored body weight, body composition change determination means for determining a change degree of the body composition value with using a comparison result of the body composition comparison means and a comparison result of the body weight comparison means, and display means for displaying a determination result determined by the body composition change determination means.

9 Claims, 5 Drawing Sheets

(56) References Cited

U.S. PATENT DOCUMENTS

| | | | |
|---|---|---|---|
| 6,354,996 B1* | 3/2002 | Drinan et al. | 600/300 |
| 6,516,221 B1 | 2/2003 | Hirouchi et al. | |
| 7,039,458 B2* | 5/2006 | Ueda et al. | 600/547 |
| 7,336,992 B2* | 2/2008 | Shiokawa | 600/547 |
| 7,979,116 B2 | 7/2011 | Tseng et al. | |
| 2001/0050683 A1 | 12/2001 | Ishikawa et al. | |
| 2004/0082877 A1* | 4/2004 | Kouou et al. | 600/546 |
| 2005/0177060 A1 | 8/2005 | Yamazaki et al. | |
| 2005/0187486 A1 | 8/2005 | Shimomura et al. | |
| 2005/0209528 A1 | 9/2005 | Sato et al. | |
| 2006/0206271 A1 | 9/2006 | Oshima et al. | |
| 2009/0204018 A1* | 8/2009 | Tseng et al. | 600/547 |

FOREIGN PATENT DOCUMENTS

| | | |
|---|---|---|
| DE | 600 11 367 T2 | 6/2005 |
| DE | 600 27 492 T2 | 4/2007 |
| EP | 1 283 024 A1 | 2/2003 |
| EP | 1 095 613 B1 | 6/2004 |
| EP | 1 576 923 A1 | 9/2005 |
| EP | 1 997 426 A1 | 12/2008 |
| JP | A-11-332845 | 12/1999 |
| JP | A-2001-190514 | 7/2001 |
| JP | A-2001-204703 | 7/2001 |
| JP | A-2004-41811 | 2/2004 |
| JP | A-2004-329225 | 11/2004 |
| JP | A-2005-077124 | 3/2005 |
| JP | A-2005-177223 | 7/2005 |
| JP | A-2005-261488 | 9/2005 |
| JP | A-2007-244728 | 9/2007 |
| WO | WO 99/52425 A2 | 10/1999 |
| WO | WO 2007/077650 A1 | 7/2007 |
| WO | WO 2007/108229 A1 | 9/2007 |

OTHER PUBLICATIONS

Russian Office Action issued in Application No. 2010142316/00(060818); Dated Sep. 20, 2011 (With Translation).

Feb. 26, 2013 Office Action issued in U.S. Appl. No. 12/866,752.

Feb. 25, 2013 Office Action issued in German Patent Application No. 11 2009 000 445.8 (with English translation).

Sep. 23, 2011 Office Action issued in Russian Patent Application No. 2010142318/14(060820) (with English translation).

Aug. 24, 2011 Office Action issued in Chinese Patent Application No. 200980108404.X (with English translation).

Jun. 16, 2009 International Search Report issued in International Application No. PCT/JP2009/055009 (with English translation).

Aug. 12, 2013 Office Action issued in German Patent Application No. 11 2009 000 519.5 (with English translation).

* cited by examiner

BODY COMPOSITION MONITOR THAT CORRECTS A BODY COMPOSITION EVALUATION BY COMPARING IT WITH A USER'S CHANGE IN WEIGHT READING TO CANCEL ERRORS CAUSED BY DRYNESS OF HANDS AND WAY OF GRIPPING

TECHNICAL FIELD

The present invention relates to a body composition monitor for calculating a body composition value from a measurement value of biological impedance, and particularly relates to a body composition monitor having a determination function of determining a degree of a change relative to a past body composition value.

BACKGROUND ART

A conventional body composition monitor is described in Patent Document 1, for example.

This Patent Document 1 discloses a body composition monitor for comparing a measured body composition value and a past measurement value so as to determine a change degree, and displaying a determination result in different colors in accordance with the change degree. Specifically, a ratio between a muscle percentage and a fat percentage is taken as an example of the body composition value. A background color of a determination display unit is changed into red when a change range is not more than −a % (the muscle percentage is decreased), green when the change range is less than ±a %, and blue when the change range is not less than +a % (the muscle percentage is increased).

Patent Document 1: Japanese Unexamined Patent Publication No. 2005-261488

DISCLOSURE OF THE INVENTION

Problems to be Solved by the Invention

However, in such a conventional body composition monitor, the body composition value such as a body fat percentage and the muscle percentage is calculated based on biological impedance. Thus, even when body composition is not changed in fact, a change in the body composition may be calculated due to an error of a value of the biological impedance caused by dryness of hand and foot skins or an unstable measuring posture. Then, a determination level is changed from the original level, and not matched with somesthesia of a user.

This invention is achieved focusing on the conventional problem described above, and an object thereof is to provide a body composition monitor capable of determining the change degree of the body composition not only by a change in the body composition value calculated based on the biological impedance but also by a change in body weight additionally so as to produce evaluation more matched with the somesthesia of the user.

Means for Solving the Problems

In order to achieve the above object, the following configurations are adopted in the present invention.

That is, a body composition monitor includes means for measuring a body composition, means for storing a measured body composition value, and body composition comparison means for comparing the measured body composition value and a stored body composition value, the body composition monitor further including means for inputting a body weight value, means for storing an inputted body weight, body weight comparison means for comparing the inputted body weight and stored body weight, body composition change determination means for determining a change degree of the body composition value with using a comparison result of the body composition comparison means and a comparison result of the body weight comparison means, and display means for displaying a determination result determined by the body composition change determination means.

According to this invention, since the change degree of the body composition value is determined not only by a change in the body composition value based on biological impedance but also by a change in the body weight additionally, stable determination can be performed without receiving an influence of an error due to measurement conditions of the biological impedance, and thereby a measured person can rightly recognize a change in his/her body composition.

When means for measuring the body weight is further provided, the body weight can also be automatically acquired and inputted.

When means for inputting at least one of age, gender and height as personal identification information of the measured person is further provided, and the body composition change determination means determines the change degree of the body composition value with further using the personal identification information, determination more matched with the measured person can be performed. For example, the body composition change determination means may be provided with a plurality of different determination criteria, and select one of the determination criteria to be used for the measured person based on the personal identification information.

When the body composition comparison means compares a plurality of different body composition values, and the body composition change determination means determines a change degree of the plurality of different body composition values, the entire tendency of a body can be obtained in comparison to a case only with the individual body composition value.

When the display means displays side by side a determination result of the change degree of the single body composition value and a determination result of the change degree of the plurality of different body composition values determined by the body composition change determination means, the entire tendency and the individual tendency of the body composition can be easily compared.

Further, when the display means displays a determination result of the change degree of the single body composition value and a determination result of the change degree of the plurality of different body composition values determined by the body composition change determination means so that both the determination results are visible at one time, the determination results can be recognized at one view.

When the display means displays the determination result and a picture shaped into a human body at one time, the determination result of a specific part of a human body can be recognized.

Examples of the body composition include a body fat amount, a body fat percentage, a subcutaneous fat amount, a subcutaneous fat percentage, a visceral fat amount, a visceral fat area, a visceral fat level, a skeletal muscle amount, and a skeletal muscle percentage.

Effect of the Invention

According to this invention, since the change degree of the body composition is determined not only by the change in the body composition value calculated based on the biological impedance but also by the change in the body weight additionally, evaluation which is more matched with somesthesia of a user can be performed.

BEST MODE FOR CARRYING OUT THE INVENTION

A preferred embodiment of this invention will be described in detail as an example with reference to the drawings.
(Configuration of Body Composition Monitor)

Figure 1:
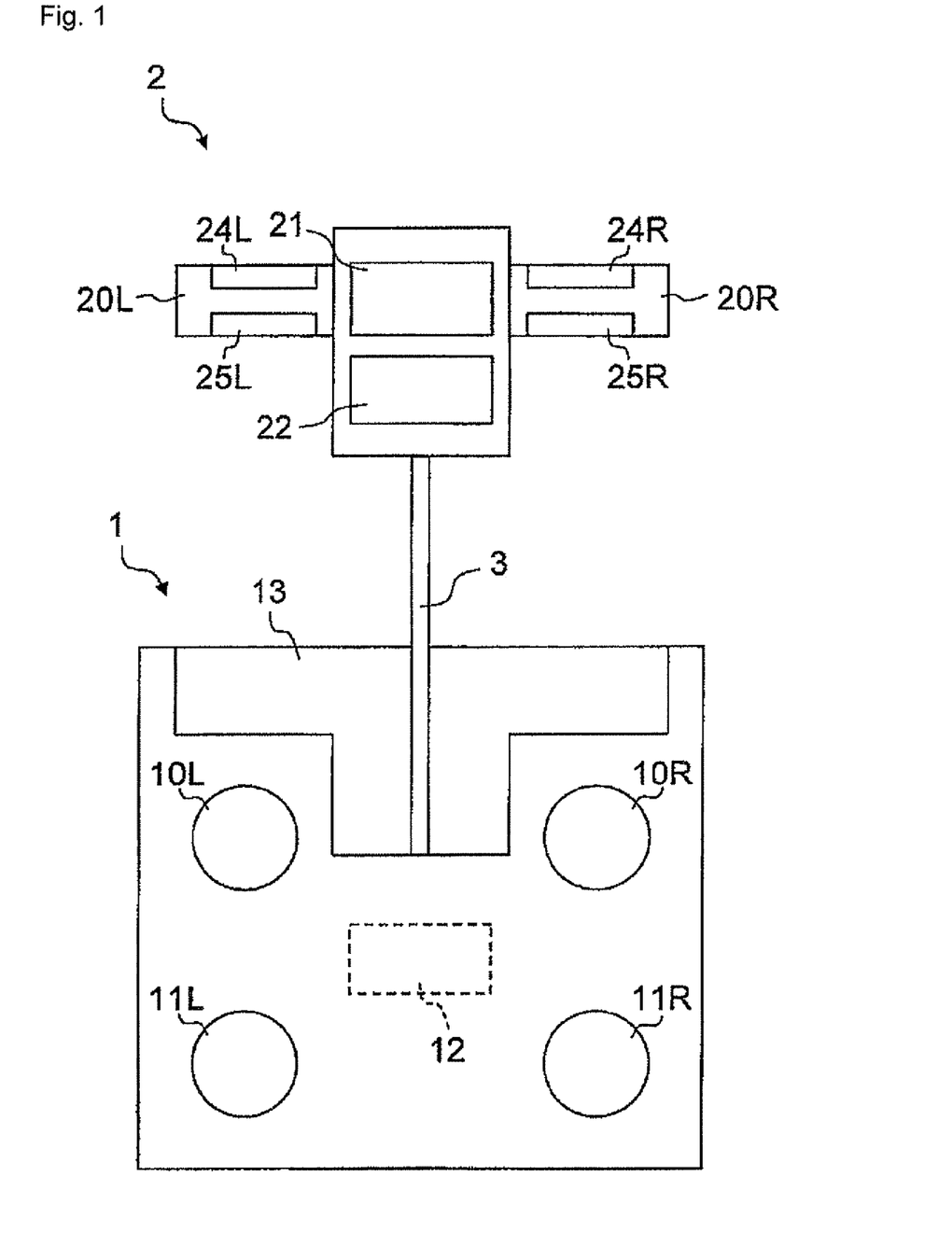
FIG. 1 is a view showing an outer appearance of a body composition monitor according to a first embodiment.

FIG. 1 shows a schematic configuration of the entire body composition monitor. A body weight and body composition monitor which is integrated with a scale will be shown as an example.

This body composition monitor is mainly formed by a main body 1, and a holder (display operation unit) 2. The main body 1 and the holder 2 are connected to each other by a cable 3 so that signals can be sent and received. It should be noted that the main body 1 and the holder 2 may be connected by wireless communication. When not used, the holder 2 and the cable 3 are accommodated in a holder accommodating unit 13 of the main body 1.

Four foot electrodes 10L, 10R, 11L, 11R are provided on an upper surface of the main body 1. The electrodes 10L, 10R are electrodes for applying an electric current to left and right foot soles, and the electrodes 11L, 11R are electrodes for detecting voltage from the left and right foot soles. A body weight measurement unit 12 serving as means for measuring body weight is built into the main body 1.

Left and right grips 20L, 20R, a display unit 21, an operation unit 22 and the like are provided in the holder 2. The display unit 21 displays a measurement result and guidance and also displays an exercise plan described later, and is for example formed by a LCD display. The operation unit 22 is provided with a user interface for selecting a registration number (user), generating and confirming the exercise plan, and inputting other information. The display unit 21 and the operation unit 22 are preferably formed by shared hardware with using a touchscreen type display.

The grips 20L, 20R are respectively provided with electrodes 24L, 24R for applying the electric current to palms and electrodes 25L, 25R for detecting the voltage from the palms.

Figure 2:
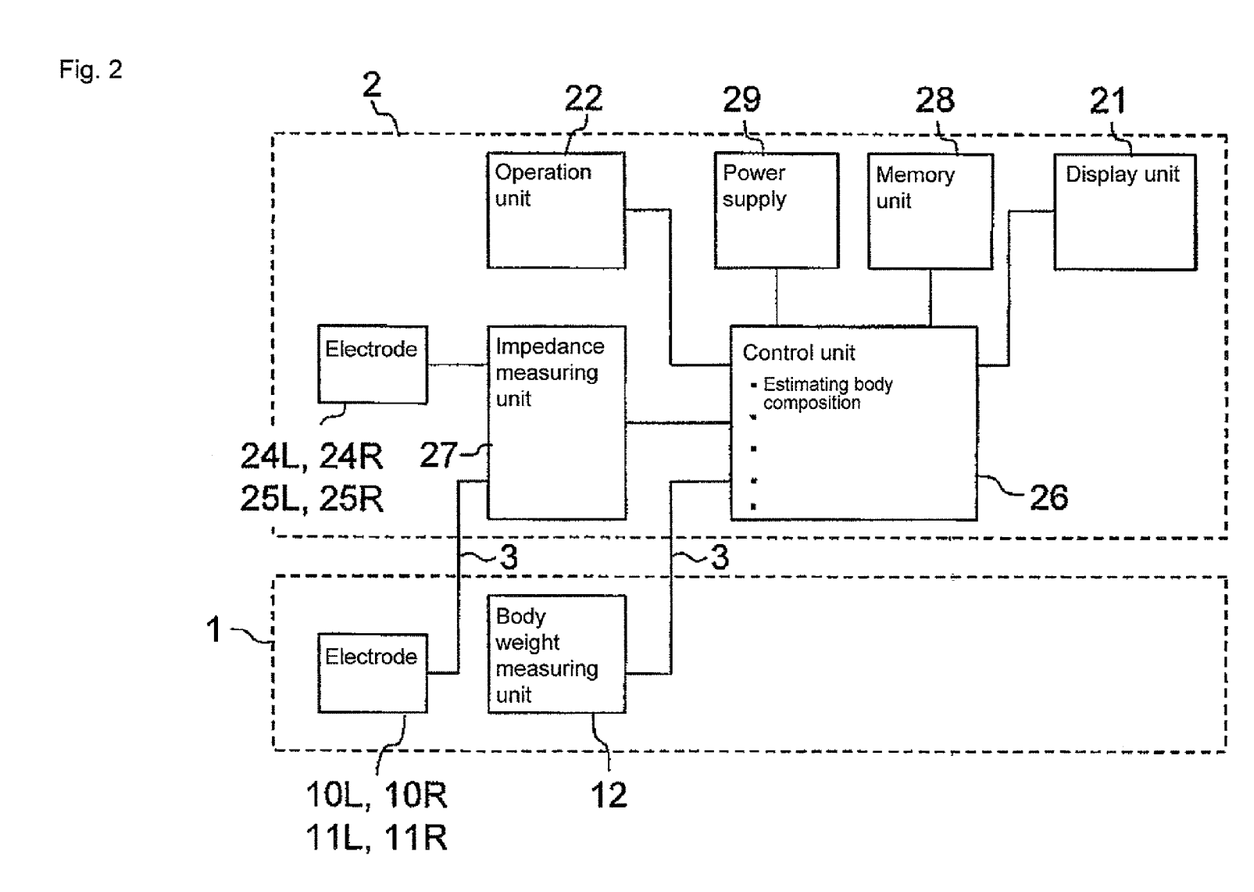
FIG. 2 is a block diagram showing a configuration of the body composition monitor in FIG. 1.

FIG. 2 is a block diagram showing a control configuration of the body composition monitor. As shown in FIG. 2, a control unit 26, an impedance measurement unit 27 serving as means for measuring a body composition, a memory unit 28, a power supply 29 and the like are built into the holder 2.

The control unit 26 has a function of storing a measured body composition value into the memory together with a measuring date and time, a body composition comparison function of comparing the measured body composition value and a stored body composition value, a function of storing a body weight value into the memory together with a measuring date and time, a body weight comparison function of comparing the measured body weight value and a stored body weight value, a body composition change determination function of determining a change degree of the body composition value with using a comparison result of the body composition and a comparison result of the body weight, and a function of outputting a determination result to the display unit 21.

The control unit 26 is formed by a CPU (central processing unit), a memory and the like, and the above functions are realized when the CPU executes a program. However, part or all of the functions of the control unit 26 may be formed by exclusive chips.

The impedance measurement unit 27 is means for applying a predetermined electric current from the foot electrodes 10L, 10R and the hand electrodes 24L, 24R to a living body in accordance with control of the control unit 26, and detecting the voltage by the foot electrodes 11L, 11R and the hand electrodes 25L, 25R so as to measure impedance inside the body. Specific functions and processing of the control unit 26 and the impedance measurement unit 27 will be described later.

The memory unit 28 is formed by a storage medium such as a nonvolatile memory. Measurement results of the body weight and the body composition (measurement values) and the like are stored in the memory unit 28 for the user (for the registration number) in chronological order by the control unit 26. Personal identification information (age, gender and height) of the user serving as a measured person is also stored in the memory unit 28.

In the body composition monitor of the present embodiment, a plurality of users (such as four users) can be registered, and any of the users can be selected by designating the registration number by the operation unit 22.
(Body Composition Measurement Function)

Figure 3:
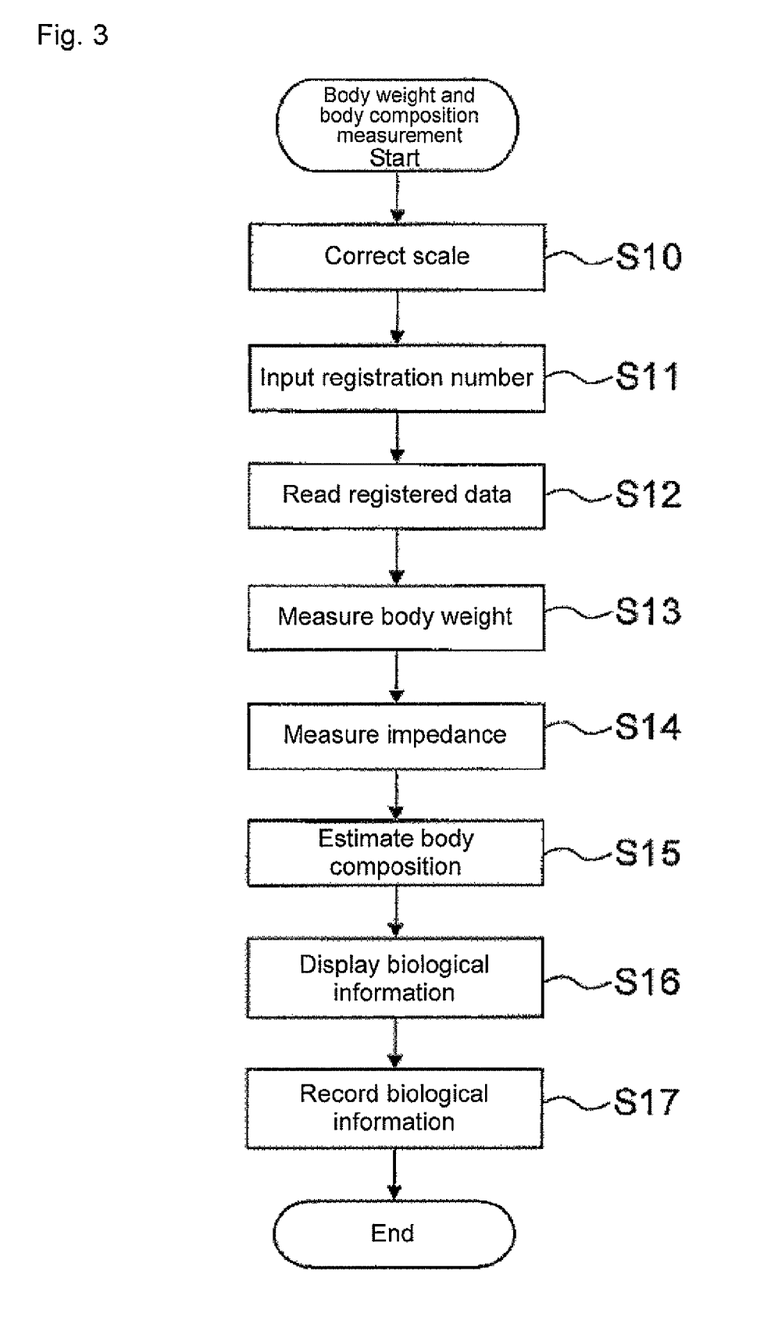
FIG. 3 is a flowchart showing a flow of measurement processing of a body weight and body composition.

With a flowchart of FIG. 3, a flow of standard processing at the time of measuring the body weight and the body composition will be described.

When the user turns ON the body composition monitor, the control unit 26 executes correction processing of a scale (Step S10). After finishing the correction, the user (registration number) can be selected. When the registration number is designated by the user (Step S11), the control unit 26 reads data related to the registration number from the memory unit 28 (Step S12).

When the user steps onto a predetermined position on the main body 1 and stands still in a measuring posture, the body weight measurement unit 12 measures the body weight (Step S13). The impedance measurement unit 27 measures impedance inside the body (Step S14). Measurement values thereof are inputted into the control unit 26.

The control unit 26 estimates the body composition based on the measurement values of the body weight and the impedance and the personal identification information read from the memory unit 28 (Step S15). As the body composition, for example, a body fat percentage, a body fat amount, a visceral fat percentage, a visceral fat amount, a subcutaneous fat percentage, and a subcutaneous fat amount can be calculated as a fat percentage and a fat amount, and a skeletal muscle percentage, a skeletal muscle amount and the like can be calculated as a muscle percentage and a muscle amount. The body composition can be calculated not only for the entire body but also for each body part such as arms, a trunk, and legs. Further, indicator information which is effective for health management and dieting such as basal metabolism, an obesity rate and body age may be generated based on the calculation results. Since the estimation of the body composition and the calculation of the indicator information can be performed by using the known methods, specific description thereof will not be provided.

The control unit 26 displays biological information such as the body weight, the body composition and the indicator information on the display unit 21 (Step S16). By looking at this display, the user can confirm the measurement results. The control unit 26 stores the biological information in the memory unit 28 together with information on measuring date and time (time stamp) (Step S17). Thereby, values of the biological information are recorded in chronological order.

The data of the body weight and the body composition value of the user stored in the memory unit 28 of one-day old, 7-days old, 30-days old, 90-days old or on a MY reference date can be read out by operating a memory key (not shown) provided in the operation unit 22 for example. The MY reference date indicates a reference date which is set by the user himself/herself.

In the present invention, the control unit 26 compares the measured body composition value and the stored body composition value, also compares the inputted body weight and the stored body weight, determines the change degree of the body composition value with using the comparison results, and displays the determination result on the display unit 21.

With regard to the comparison between the measured body composition value and the stored past body composition value, a difference between the latest body composition value and the past body composition value is determined and compared with a preliminarily set threshold value so as to determine an evaluation level as the comparison result. The evaluation level is basically divided into three stages including status quo, a good change, and a bad change but may be divided into two stages or four stages or more.

With regard to the comparison between the measured body weight and the stored past body weight, a difference between the latest measured body weight and the past body weight is also determined and compared with a preliminarily set threshold value so as to determine an evaluation level as the comparison result. The evaluation level is basically divided into three stages including status quo, a good change, and a bad change but may be divided into two stages or four stages or more.

With regard to the comparison, for example, when a memory switch is pressed and the past measurement data is read out, the difference from the latest measurement data is calculated and compared with the threshold value so as to determine the evaluation level. The change degree of the body composition value is determined with using the comparison results of the body composition value and the body weight, and the determination result is outputted to the display unit.

The measurement values of the body composition values are changed in accordance with measurement values of the impedance which are varied due to dryness of the hands and the way of gripping. Thus, even when the evaluation level of the body composition value is determined to be favorable, the favorable result may be produced due to a measurement error, and the evaluation level may not correspond to somesthesia. Meanwhile, the body weight is an absolute factor irrespective of the dryness and the way of gripping, and thus the evaluation level of the body composition value is corrected by combining with a change evaluation of the body weight. For example, even when an evaluation level of a skeletal muscle percentage change is favorable but the body weight change is large on the positive side, a measurement value of the skeletal muscle percentage is supposed to be increased due to the measurement error. Thus, the evaluation level is corrected to be lower, and a display signal is outputted to the display unit in accordance with the final evaluation level, so that the evaluation level is displayed on the display unit.

With regard to the determination, the body composition values cannot uniformly be evaluated due to the personal identification information such as age, gender, height and body weight. Thus, at least one of age, gender and height is inputted as the personal identification information of the user, and the inputted personal identification information is further used so as to determined the change degree of the body composition value. The personal identification information is for example inputted by operating a key provided in the operation unit 22, and the operation unit 22 serves as input means for the personal identification information.

Specifically, a plurality of determination criteria according to age, gender, height and the like is set, and the relevant determination criterion is selected based on the personal identification information of the user serving as the measured person. The determination criteria are stored in the memory unit 28 as evaluation tables. In this example, when the registration number is designated, the personal identification information (age, gender or height) related to the registration number is read out from the memory unit 28 (refer to S11, S12 in FIG. 3), and the determination criterion to be used by the user is selected based on the personal identification information. The personal identification information may be one of or a combination of age, gender and height, but should be the determination criterion based on at least one type of personal identification information.

The comparison of the body composition in the control unit 26 indicates comparison of not only the individual body composition value but also a plurality of different body composition values. The determination of the body composition change also indicates determination of a change degree of the plurality of different body composition values. Examples of the comparison of the plurality of different body composition values include comparison between a ratio between the skeletal muscle percentage and the subcutaneous fat percentage or the skeletal muscle percentage and the visceral fat level for example.

Table 1 is an example of a change evaluation table of the skeletal muscle percentage, and Table 2 is an example of a table made by simplifying the change evaluation table of Table 1.

The change evaluation of the skeletal muscle percentage or the body weight basically includes three stages of Favorable (⊙, ○), status quo (▲) and Unfavorable (x), and Favorable is divided into two stages of Favorable 2 (⊙) and Favorable 1 (○) so as to motivate the user. In order to divide into four stages, three stages of the threshold value are set.

The skeletal muscle percentage indicates a ratio of skeletal muscles in the body weight. In general, when fat is reduced in dieting, the skeletal muscle percentage is increased. Therefore, a case where a change percentage is decreased (negative) is indicated as Unfavorable, and a case where the change percentage is increased (positive) is indicated as Favorable. In Table 1, three threshold values of −0.2%, +0.1% and +0.25% are set.

Body weight increase is generally not preferable. Thus, a case where a change percentage is increased (positive) is indicated as Unfavorable, and a case where the change percentage is decreased (negative) is indicated as Favorable. Three threshold values of +5%, −2% and −5% are set.

The measurement value of the skeletal muscle percentage is changed due to the dryness of the hands. Thus, even when the skeletal muscle percentage is determined to be Favorable 2 (⊙) or 1 (○), the favorable result may be produced due to the measurement error, and the result may not correspond to the somesthesia. Meanwhile, the body weight is the absolute factor irrespective of environmental factors such as the dryness of the skin, and thus the change evaluation of the skeletal muscle percentage is corrected by combining with the change evaluation of the body weight.

For example, even when individual determination of the skeletal muscle percentage change is Favorable 2 (☉) but the body weight change is evaluated as Unfavorable (x), the measurement value of the skeletal muscle percentage is supposed to be increased due to the measurement error of the impedance. Thus, the determination is corrected to be at least one-stage lower level, status quo (▲) or Unfavorable (x).

With regard to selection of Unfavorable (x), the threshold values of the body weight or the skeletal muscle percentage are divided more so as to match the determination with the somesthesia.

On the other hand, even when the individual determination of the skeletal muscle percentage is status quo (▲) but the body weight change is evaluated as Favorable 2 (☉) or Favorable 1 (o), the determination is corrected to be Favorable 1 (o) or status quo (▲). This is because the measurement value of the skeletal muscle percentage is supposed to be decreased due to the measurement error of the impedance.

With regard to selection of Favorable (o), the threshold values of the body weight or the skeletal muscle percentage are divided more so as to match the determination with the somesthesia.

Table 3 is an example of a change evaluation table of the ratio between the skeletal muscle percentage and the subcutaneous fat percentage for comparing a plurality of different body composition, and Table 4 is an example of a table made by simplifying Table 3. This ratio is calculated by "skeletal muscle percentage/(skeletal muscle percentage+subcutaneous fat percentage)". Change evaluation thereof basically includes four stages of Favorable (☉, o), status quo (▲) and Unfavorable (x).

In general, when the body weight is reduced in dieting, subcutaneous fat is reduced. Thus, the ratio between the skeletal muscle percentage and the subcutaneous fat percentage is increased. Therefore, a case where a change percentage is decreased (negative) is indicated as Unfavorable, and a case where the change percentage is increased (positive) is indicated as Favorable. Three threshold values of (−3%), (+1%) and (+4%) are set.

The measurement values of this ratio are also changed in accordance with the measurement values of the impedance which are varied due to the dryness of the hands and the way of gripping. Thus, even when the result is determined to be Favorable (☉) (o), the favorable result may be produced due to the measurement error of the impedance, and the change evaluation of the skeletal muscle percentage is corrected by combining with the change evaluation of the body weight.

For example, even when the change in the ratio between the skeletal muscle percentage and the subcutaneous fat percentage is evaluated as Favorable 2 (☉) but the body weight change is evaluated as Unfavorable (x), the favorable result is supposed to be produced due to the measurement error. Thus, the determination is corrected to be status quo (▲) or Unfavorable (x).

Table 5 is an example of a change evaluation table of the visceral fat level, and Table 6 is an example of a table made by simplifying Table 5. The change evaluation of this visceral fat level basically includes four stages of Favorable (☉, o), status quo (▲) and Unfavorable (x).

The visceral fat level is an indicator for sectional areas of the visceral fat, including one to 30 levels at 0.5 intervals. The change evaluation thereof basically includes four stages of Favorable (☉, o), status quo (▲) and Unfavorable (x).

In general, when the body weight is reduced in dieting, the visceral fat level is reduced. Thus, a case where the visceral fat level is increased is indicated as Unfavorable, and a case where the visceral fat level is decreased is indicated as Favorable. Three threshold values of (+3 level), (−1.5 level) and (−3.5 level) are set.

The measurement values thereof are also changed in accordance with the measurement values of the impedance which are varied due to the dryness of the hands and the way of gripping. Thus, even when the result is determined to be Favorable (☉) (o), the favorable result may be produced due to the measurement error of the impedance, and the change evaluation is corrected by combining with the change evaluation of the body weight.

For example, even when individual determination of the visceral fat level in Table 5 is Favorable 2 (☉) but the body weight change is evaluated as Unfavorable (x), the measurement value is supposed to be decreased due to the measurement error of the impedance. Thus, the determination is corrected to be status quo (▲) or Unfavorable (x).

The determination tables of Tables 1 to 6 are varied for example in accordance with gender, age, height and the like, and determination tables are produced for each gender and each age and stored in the memory unit 28. The corresponding evaluation tables are referred in accordance with registered data of the user, so that the change in the body composition is determined.

The control unit 26 outputs change evaluation results of the body composition determined as above, and displays the results on the display unit 21.

Figure 4:
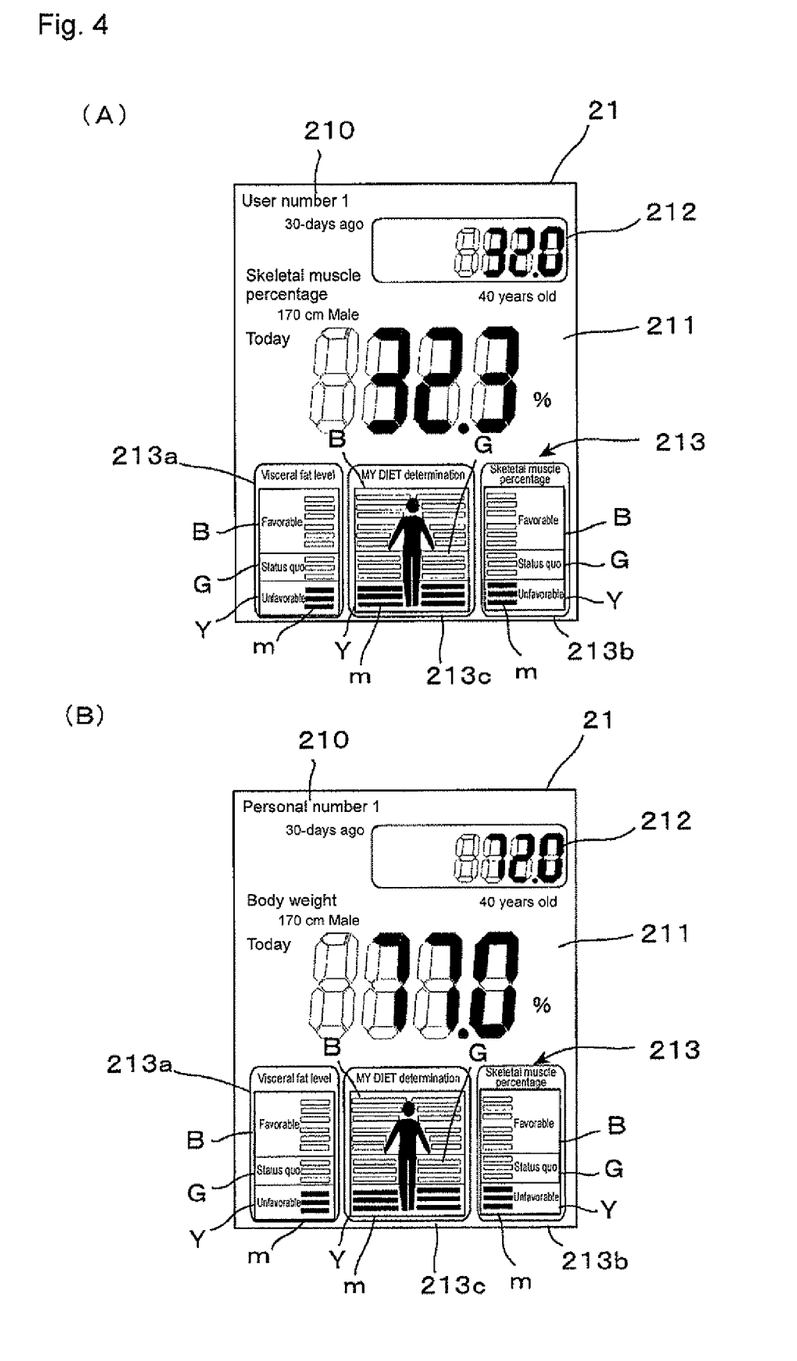
FIGS. 4(A) and 4(B) show one example of a screen configuration of a display unit.

Firstly, with reference to FIG. 4, a screen configuration of the display unit 21 will be briefly described.

A user number 210, a measurement data display field 211 of current measurement data, a measurement data display field 212 of past measurement data stored in the memory unit 28, and a determination display field 213 of the body composition are provided in the display unit 21.

Three fields including a visceral fat level determination display field 213a and a skeletal muscle percentage determination display field 213b for the determination results of the change degree of the single body composition value, and a MY DIET determination display field 213c showing the ratio between the skeletal muscle percentage and the subcutaneous fat percentage for the determination result of the change degree of the plurality of different body composition values are provided in the determination display field 213.

In the determination display fields 213a, 213b, 213c, the determination results are displayed by three lines of display marks m in a Favorable area B, a status quo area G, and a Unfavorable area Y. The Favorable area B is divided into a Favorable 2 area B 1 and a Favorable area $B^2$.

The determination result and a human icon serving as a picture shaped into a human body are displayed on the MY DIET determination display field 213c, and a body part such as arms, legs, and a trunk can be displayed.

Next, the display of this display unit 21 will be briefly described.

With regard to the measurement data of the user, current body weight is firstly displayed on the measurement data display field 211. When a display switch key (not shown) is pressed, the kind of the body composition displayed on the measurement data display field 211 of the current measurement data is switched. Meanwhile, when a memory key (not shown) is pressed, the past measurement data of the body composition is read out from the memory unit 28 and displayed on the measurement data display field 212 of the past measurement data. The display is switched to show the past measurement data of one-day old, 7-days old, 30-days old, 90-days old and on the MY reference date, respectively. The MY reference date indicates a reference date which is set by the user himself/herself. The display may be automatically switched without the memory key.

A difference between the current measurement data and the past measurement data is calculated and a difference between the measurement data of the body weight is calculated. Then, the corresponding determination table stored in the memory is read out, the change amounts of the body composition and the body weight are compared with the threshold values of the determination table so as to select the corresponding determination result, and a determination signal is generated and outputted based on the determination result. Based on the outputted determination signal, the display mark m is displayed on the corresponding evaluation area (the Favorable area B, the status quo area G or the Unfavorable area Y) of the determination display field of the display unit 21. At this time, the light may be emitted on the background color.

For example, in FIG. 4, the skeletal muscle percentage is selected as the kind of the measurement data, and the current measurement data is 32.3%. When the skeletal muscle percentage of 30-days old is 32.0% in FIG. 4(A), the single determination of the skeletal muscle percentage is Favorable 2 (◯) with increase of +0.3% referring to Table 1. However, when the body weight is increased from 72 kg to 77 kg as shown in FIG. 4(B), the body weight is increased by not less than 5%, so that the evaluation level is status quo (▲) or Unfavorable (x). In the illustrated example, the evaluation level is Unfavorable (x).

When the body weight is increased by 5 kg, the user feels gaining the body weight as the somesthesia. The determination of the skeletal muscle percentage to be Favorable (◯) is not matched with the somesthesia. At this point, when the evaluation of the body weight is added, the determination result is close to the determination result.

In the illustrated example, not only the determination result is displayed on the skeletal muscle percentage determination display field 213b but also the change amounts of the measurement data regarding the visceral fat level and the MY DIET determination are calculated at one time and the determination results are displayed on the visceral fat level determination display field 213a and the MY DIET determination display field 213c which is a display field of the change degree of the plurality of different body composition values at one time.

However, the results are not necessarily displayed all together. Only the determination result of the displayed body composition, that is, the skeletal muscle percentage in this example, may be displayed.

Figure 5:
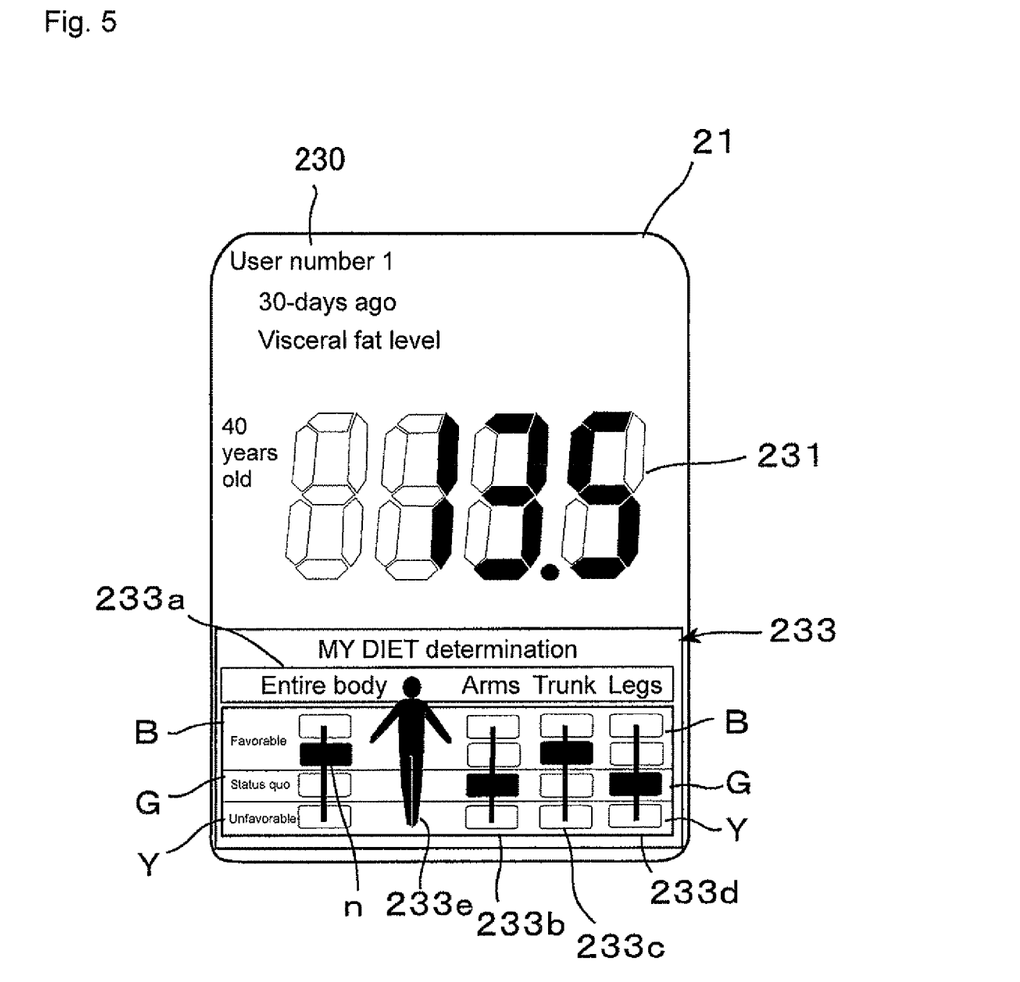
FIG. 5 is a view showing another screen configuration example of the display unit.

FIG. 5 shows another screen configuration example of the display unit 21.

A personal number 230 of the user, a data display field 231 and a determination display field 233 of the body composition are provided in the display unit 21.

In the illustrated example, determination display fields 233a, 233b, 233c, 233d are respectively provided for four body parts including the entire body, the arms, the trunk, and the legs, and a human icon 233e is displayed. In the illustrated example, only the MY DIET determination regarding the ratio between the skeletal muscle percentage and the subcutaneous fat percentage for the determination result of the change degree of the plurality of different body composition values is available as the body composition to be determined. As a matter of course, change amounts of other body composition may be determined.

The rectangular display marks m are displayed on the Favorable area B, the status quo area G and the Unfavorable area Y on the determination display fields 233a, 233b, 233c, 233d. The light may be emitted or blinked for each of the body parts including the arms, the legs, and the trunk of the human icon 233e so as to distinguish evaluation contents.

In this example, the ratio between the skeletal muscle percentage and the subcutaneous fat percentage for each of the body parts including the entire body, the arms, the trunk, and the legs is calculated from the measured impedance as the body composition and stored in the memory 28 as the measurement data together with the measuring date and time.

The data on the measurement data display field 231 is switched to the data of one-day old, 7-days old, 30-days old, 90-days old and on the MY reference date, respectively, by switching the memory key or the like (not shown). The visceral fat level is displayed on the data display field 231 in the illustrated example. However, the body weight may be displayed or other body composition may be displayed.

The change amount between the current data and the past data of the ratio between the skeletal muscle percentage and the subcutaneous fat percentage for each of the body parts and the body weight change amount are calculated in accordance with this reference date, and the determination table read out from the memory unit 28 is referred so as to determine the evaluation level. The determination table is not particularly shown but made by combining the change in the ratio between the skeletal muscle percentage and the subcutaneous fat percentage for each of the body part as well as Table 3 and the change in the body weight.

The display signal is outputted in accordance with this evaluation level, and the display mark is displayed on the corresponding evaluation area for each of the body parts on the MY DIET determination display field. The light may be blinked or emitted for the corresponding part of the human icon at the same time.

It should be noted that the above embodiment only shows one specific example of the present invention. The scope of the present invention is not limited to the above embodiment but may be variously modified within the technological scope thereof.

For example, in the above embodiment, the skeletal muscle percentage, the ratio between the skeletal muscle percentage and the subcutaneous fat percentage, and the visceral fat level are described as examples of the body composition values. However, any of the fat amount, the muscle amount, the fat percentage and the muscle percentage may be described, and various body composition information which is related to the body weight such as the subcutaneous fat amount, the subcutaneous fat percentage, the visceral fat amount, the visceral fat percentage, and the skeletal muscle amount can be selected. The processing flow and the display screens in the above embodiment are only one specific example and may be appropriately modified as long as similar results and effects can be obtained.

TABLE 1

| Skeletal muscle percentage | | Body weight | | Corrected determination |
|---|---|---|---|---|
| X | (to −0.2%) | X | (from +5%) | X |
|  |  | ▲ | (−2 to +5%) | X |
|  |  |  |  | ▲ |

TABLE 1-continued

| Skeletal muscle percentage | | Body weight | Corrected determination |
|---|---|---|---|
| | ⊙ | (−5% to −2%) | X |
| | | | ▲ |
| | ⊙ | (to −5%) | X |
| | | | ▲ |
| ▲ (−0.2% to +0.1%) | X | (from +5%) | X |
| | ▲ | (−2 to +5%) | ▲ |
| | ○ | (−5% to −2%) | ▲ |
| | | | ○ |
| | ⊙ | (to −5%) | ▲ |
| | | | ○ |
| ○ (+0.1% to +0.25%) | X | (from +5%) | X |
| | ▲ | (−2 to +5%) | ▲ |
| | | | ○ |
| | ○ | (−5% to −2%) | ○ |
| | ⊙ | (to −5%) | ○ |
| | | | ⊙ |
| ⊙ (from +0.25%) | X | (from +5%) | X |
| | | | ▲ |
| | ▲ | (−2 to +5%) | ○ |
| | | | ⊙ |
| | ○ | (−5% to −2%) | ⊙ |
| | ⊙ | (to −5%) | ⊙ |

TABLE 2

| | | | | Body weight | | | | |
|---|---|---|---|---|---|---|---|---|
| | | ⊙ | | ○ | | ▲ | | X |
| Skeletal muscle percentage | ⊙ | ⊙ | | ⊙ | | ⊙ | ⊙ ○ | ▲ X |
| | ○ | ○ | ⊙ | ○ | | ○ | ○ ▲ | X |
| | ▲ | ▲ | ○ | ▲ | ○ | ▲ | ▲ | X |
| | X | X | ▲ | X | ▲ | X | ▲ X | X |

TABLE 3

| Ratio between skeletal muscle percentage and subcutaneous fat percentage | | Body weight | Corrected determination |
|---|---|---|---|
| X (to −3%) | X | (from +5%) | X |
| | ▲ | (−2 to +5%) | X |
| | | | ▲ |
| | ○ | (−5% to −2%) | X |
| | | | ▲ |
| | ⊙ | (to −5%) | X |
| | | | ▲ |
| ▲ (−3% to +1%) | X | (from +5%) | X |
| | ▲ | (−2 to +5%) | ▲ |
| | ○ | (−5% to −2%) | ▲ |
| | | | ○ |
| | ⊙ | (to −5%) | ▲ |
| | | | ○ |
| ○ (+1% to +4%) | X | (from +5%) | X |
| | ▲ | (−2 to +5%) | ▲ |
| | | | ○ |
| | ○ | (−5% to −2%) | ○ |
| | ⊙ | (to −5%) | ○ |
| | | | ⊙ |
| ⊙ (from +4%) | X | (from +5%) | X |
| | | | ▲ |
| | ▲ | (−2 to +5%) | ○ |
| | | | ⊙ |
| | ○ | (−5% to −2%) | ⊙ |
| | ⊙ | (to −5%) | ⊙ |

TABLE 4

| | Body weight determination | | | |
|---|---|---|---|---|
| | ⊙ | ○ | ▲ | X |
| Skeletal muscle percentage/ (skeletal muscle percentage + subcutaneous fat percentage) | ⊙ ○ ▲ X | ⊙ ⊙ ○ ▲ | ⊙ ○ ▲ X | ⊙ ⊙ ○ ▲ ○ ▲ X ▲ X ▲ X X |

TABLE 5

| Visceral fat level | | Body weight | | Corrected determination |
|---|---|---|---|---|
| X | (from +3 level) | X | (from +5%) | X |
| | | ▲ | (−2 to +5%) | X |
| | | | | ▲ |
| | | ○ | (−5% to −2%) | X |
| | | | | ▲ |
| | | ⊙ | (to −5%) | X |
| | | | | ▲ |
| ▲ | (−3 level to −1.5 level) | X | (from +5%) | X |
| | | ▲ | (−2 to +5%) | ▲ |
| | | ○ | (−5% to −2%) | ▲ |
| | | | | ○ |
| | | ⊙ | (to −5%) | ▲ |
| | | | | ○ |
| ○ | (−1.5 level to −3.5 level) | X | (from +5%) | X |
| | | ▲ | (−2 to +5%) | ▲ |
| | | | | ○ |
| | | ○ | (−5% to −2%) | ○ |
| | | ⊙ | (to −5%) | ○ |
| | | | | ⊙ |
| ⊙ | (to −3.5 level) | X | (from +5%) | X |
| | | | | ▲ |
| | | ▲ | (−2 to +5%) | ○ |
| | | | | ⊙ |
| | | ○ | (−5% to −2%) | ⊙ |
| | | ⊙ | (to −5%) | ⊙ |

TABLE 6

| | | | | Body weight | | | | |
|---|---|---|---|---|---|---|---|---|
| | | ⊙ | | ○ | | ▲ | | X |
| Visceral fat level | ⊙ | ⊙ | | ⊙ | | ⊙ | ⊙ ○ | ▲ X |
| | ○ | ○ | ⊙ | ○ | | ○ | ○ ▲ | X |
| | ▲ | ▲ | ○ | ▲ | ○ | ▲ | ▲ | X |
| | X | X | ▲ | X | ▲ | X | ▲ X | X |

DESCRIPTION OF SYMBOLS

1 main body
2 holder
3 cable
10L, 10R, 11L, 11R foot electrode
12 body weight measurement unit
13 holder accommodating unit
20L, 20R grip
21 display unit
22 operation unit
24L, 24R, 25L, 25R hand electrode
26 control unit
27 impedance measurement unit
28 memory unit
29 power supply
210 user number
211 display field of current measurement data
212 display field of past measurement data 213 determination display field
213a determination display field (visceral fat level)
213b determination display field (skeletal muscle percentage)
213c determination display field (MY DIET)
233 determination display field of body composition
233a determination display field (entire body)
233b determination display field (arms)
233c determination display field (trunk)
233d determination display field (legs)
B favorable
G status quo
Y unfavorable

The invention claimed is:

1. A body composition monitor, comprising:
means for measuring a body composition;
means for storing a measured body composition value; and
body composition comparison means for comparing the measured body composition value and a stored body composition value, wherein the body composition comparison means determines a body composition evaluation level by comparing a difference between the measured body composition value and the stored composition value with a first predetermined threshold value,
the body composition monitor further comprising:
means for inputting a body weight value;
means for storing an inputted body weight; and
body weight comparison means for comparing the inputted body weight and the stored body weight, wherein the body weight comparison means determines a body weight evaluation level by comparing a difference between the inputted body weight and the stored body weight with a second predetermined threshold value,
the body composition monitor further comprising:
body composition change determination means for determining a corrected body composition evaluation level by comparing the body composition evaluation level with the body weight evaluation level; and
display means for displaying the corrected body composition evaluation level.

2. The body composition monitor according to claim 1, wherein the means for inputting a body weight value comprises means for measuring the body weight.

3. The body composition monitor according to claim 1, further comprising:
means for inputting at least one of age, gender and height as personal identification information of a measured person, wherein
the body composition change determination means determines the corrected body composition evaluation level by using the personal identification information.

4. The body composition monitor according to claim 3, wherein the body composition change determination means is provided with a plurality of different determination criteria, and selects one of the determination criteria to be used for the measured person based on the personal identification information.

5. The body composition monitor according to claim 1, wherein the body composition comparison means compares a plurality of different body composition values, and the body composition change determination means determines a corrected body composition evaluation level for each of the plurality of different body composition values.

6. The body composition monitor according to claim 5, wherein the display means displays side by side the corrected body composition evaluation level for each of the plurality of different body composition values determined by the body composition change determination means.

7. The body composition monitor according to claim 5, wherein the display means displays the corrected body composition evaluation level for each of the plurality of different body composition values determined by the body composition change determination means so that the corrected body composition evaluation level for each of the plurality of different body composition values are visible at one time.

8. The body composition monitor according to claim 1, wherein the display means displays the corrected body composition evaluation level and a picture shaped into a human body at one time.

9. The body composition monitor according to claim 1, wherein the body composition indicates a body fat amount, a body fat percentage, a subcutaneous fat amount, a subcutaneous fat percentage, a visceral fat amount, a visceral fat area, a visceral fat level, a skeletal muscle amount, or a skeletal muscle percentage.

* * * * *